US009470660B2

(12) United States Patent
Dunne et al.

(10) Patent No.: US 9,470,660 B2
(45) Date of Patent: Oct. 18, 2016

(54) PIEZOELECTRIC SENSOR CONFIGURATION FOR DETECTING DAMAGE IN A STRUCTURE

(71) Applicant: The Boeing Company, Chicago, IL (US)

(72) Inventors: James P. Dunne, Ballwin, MO (US);
Jeong-Beom Ihn, Bellevue, WA (US);
Lawrence E. Pado, St. Charles, MO (US)

(73) Assignee: The Boeing Company, Chicago, IL (US)

( * ) Notice: Subject to any disclaimer, the term of this patent is extended or adjusted under 35 U.S.C. 154(b) by 214 days.

(21) Appl. No.: 14/282,577

(22) Filed: May 20, 2014

(65) Prior Publication Data

US 2015/0338306 A1    Nov. 26, 2015

(51) Int. Cl.
*G01N 29/04*   (2006.01)
*G01M 5/00*    (2006.01)
*G01N 29/24*   (2006.01)

(52) U.S. Cl.
CPC ............ *G01N 29/04* (2013.01); *G01M 5/0033* (2013.01); *G01M 5/0066* (2013.01); *G01N 29/2437* (2013.01)

(58) Field of Classification Search
CPC ..................... G01N 29/04; G01N 29/2437
USPC ............................................. 73/628
See application file for complete search history.

(56) References Cited

U.S. PATENT DOCUMENTS

| 8,286,492 | B2* | 10/2012 | Sohn | G01N 29/041 73/602 |
| 2010/0206081 | A1* | 8/2010 | Jones | G01N 29/043 73/620 |
| 2012/0255359 | A1* | 10/2012 | Sohn | G01N 29/043 73/598 |

* cited by examiner

*Primary Examiner* — John Chapman, Jr.
(74) *Attorney, Agent, or Firm* — Kunzler Law Group, PC

(57) ABSTRACT

Described herein is an apparatus for detecting damage in a structure that includes a plurality of first piezoelectric sensing elements arranged in a generally circular shape. The apparatus also includes an annular-shaped second piezoelectric sensing element positioned adjacent the plurality of first piezoelectric sensing elements. One of the plurality of first piezoelectric sensing elements or the annular-shaped second piezoelectric sensing element generates a wave through the structure and other of the plurality of first piezoelectric sensing elements or the annular-shaped second piezoelectric sensing element senses the wave after passing through the structure.

20 Claims, 6 Drawing Sheets

PIEZOELECTRIC SENSOR CONFIGURATION FOR DETECTING DAMAGE IN A STRUCTURE

FIELD

This disclosure relates generally to detecting damage in a structure, and more particularly to detecting cracks in a structure using a piezoelectric sensor configuration.

BACKGROUND

Structures experiencing loads or exposed to various environmental factors are susceptible to damage, such as cracking, corrosion, delamination, and the like. Damage to structures may lead to aesthetic flaws, structural degradation, inefficiencies, poor performance, and even catastrophic failure. Accordingly, the detection of damage to structures may be desirable to mitigate or prevent the occurrence of such negative consequences. In some circumstances, the negative consequences of damage to the structure can be mitigated or prevented through detection and repair of the damage.

Some structures include features that are particularly susceptible to damage or the inducement of damage. For example, cracks tend to form at and emanate from fastener holes in surfaces of certain structures, such as aircraft.

SUMMARY

The subject matter of the present application has been developed in response to the present state of the art, and in particular, in response to the problem of, and the need to, detect damage, such as crack formations, in various structures, such as aircraft, that have not yet been fully solved by currently available techniques. Once disassembled, conventional detection methods, such as non-destructive ultrasonic testing techniques, may be used to detect such damage. The time and effort associated with disassembly, ultrasonic testing, and reassembly of some structures using conventional techniques can be overly burdensome in both time and cost. In contrast, some detection techniques use an arrangement of piezoelectric elements positioned in situ about a hole formed in the structure. However, such conventional in situ techniques rely on a rectangular or side bank arrangement of piezoelectric elements relative to the hole, which fails to provide an adequate or comprehensive detection of damage in the structure proximate the hole. Accordingly, the subject matter of the present application has been developed to provide an apparatus, system, and method for detecting damage in a structure that overcome at least some of the above-discussed shortcomings of prior art techniques.

According to one embodiment, an apparatus for detecting damage in a structure includes a plurality of first piezoelectric sensing elements arranged in a generally circular shape. The apparatus also includes an annular-shaped second piezoelectric sensing element positioned adjacent the plurality of first piezoelectric sensing elements. One of the plurality of first piezoelectric sensing elements or the annular-shaped second piezoelectric sensing element generates a wave through the structure. The one of the plurality of first piezoelectric sensing elements or the annular-shaped second piezoelectric sensing element can include all (or one or some) of the first piezoelectric sensing elements or the annular-shaped second piezoelectric sensing element. Other of the plurality of first piezoelectric sensing elements or the annular-shaped second piezoelectric sensing element senses the wave after passing through the structure. The other of the plurality of first piezoelectric sensing elements or the annular-shaped second piezoelectric sensing element can include all (or one or some) of the plurality of first piezoelectric sensing elements or the annular-shaped second piezoelectric sensing element.

In certain implementations of the apparatus, the annular-shaped second piezoelectric sensing element surrounds the plurality of first piezoelectric sensing elements.

According to some implementations, the apparatus also includes a plurality of third piezoelectric sensing elements arranged in a generally circular shape surrounding the annular-shaped second piezoelectric sensing element. Additionally, the apparatus may include an annular-shaped fourth piezoelectric sensing element that surrounds the plurality of third piezoelectric sensing elements. In one implementation, the plurality of first piezoelectric sensing elements includes at least five piezoelectric sensing elements.

In some implementations of the apparatus, the plurality of first piezoelectric sensing elements and the annular-shaped second piezoelectric sensing element are bonded onto the structure. The apparatus may include a plurality of electrical lead pairs bonded to the structure. Each of the plurality of electrical lead pairs includes at least two electrical leads electrically coupled to a respective one of the first and second piezoelectric sensing elements.

According to one implementation, the apparatus includes a mobile test head that is movable along the structure. The mobile test head includes the plurality of first piezoelectric sensing elements and the annular-shaped second piezoelectric sensing element.

In certain implementations of the apparatus, the plurality of first piezoelectric sensing elements and the annular-shaped second piezoelectric sensing element collectively define a first sensing element group. The apparatus also includes a second sensing element group that is spaced apart from the first sensing element group. The second sensing element group includes a plurality of third piezoelectric sensing elements arranged in a generally circular shape and an annular-shaped fourth piezoelectric sensing element positioned adjacent the plurality of second piezoelectric sensing elements. One of the plurality of first piezoelectric sensing elements and the annular-shaped second piezoelectric sensing element generates a wave through the structure and one of the plurality of third piezoelectric sensing elements and the annular-shaped fourth piezoelectric sensing element senses the wave after passing through the structure. The first sensing element group can be centered around a first hole formed in the structure and the second sensing element group can be centered around a second hole formed in the structure. The apparatus may also include a controller that is configured to selectively switch between operation in a first mode and second mode. In the first mode, the controller activates the first sensing element group to generate a first wave and receives input from the first sensing element group regarding characteristics of the first wave and activates the second sensing element group to generate a second wave and receives input from the second sensing element group regarding characteristics of the second wave. In the second mode, the controller activates the first sensing element group to generate a third wave and receives input from the second sensing element group regarding characteristics of the third wave.

According to some implementations, the apparatus further includes a controller that is configured to activate the one of the plurality of first piezoelectric sensing elements or the annular-shaped second piezoelectric sensing element to generate the wave, and to receive input from other of the plurality of first piezoelectric sensing elements or the annular-shaped second piezoelectric sensing element that sense the wave after passing through the structure. The apparatus can also include a plurality of electrical lead pairs bonded to the structure. Each of the plurality of electrical lead pairs can include at least two electrical leads electrically coupled to a respective one of the first and second piezoelectric sensing elements. The controller includes an electrical lead interface that interfaces with the plurality of electrical lead pairs to send electrical signals to or receive electrical signals from the plurality of first piezoelectric sensing elements and the annular-shaped second piezoelectric sensing element.

In certain implementations, the annular-shaped second piezoelectric sensing element is substantially coaxial with the generally circular shape of the plurality of first piezoelectric sensing elements. The annular-shaped second piezoelectric sensing element can be positioned radially outwardly away from the plurality of first piezoelectric sensing elements. According to some implementations, each of the first piezoelectric sensing elements includes a piezoelectric sensor disc.

According to another embodiment, a system includes a structure with a hole. The system also includes a plurality of first piezoelectric sensing elements bonded to the structure and arranged in a generally circular shape about the hole. Additionally, the system includes an annular-shaped second piezoelectric sensing element bonded to the structure. The annular-shaped second piezoelectric sensing element is positioned adjacent the plurality of first piezoelectric sensing elements and about the hole. One of the plurality of first piezoelectric sensing elements or the annular-shaped second piezoelectric sensing element generates a wave through the structure and other of the plurality of first piezoelectric sensing elements or the annular-shaped second piezoelectric sensing element senses the wave after passing through the structure adjacent the hole.

In some implementations of the system, each of the plurality of first piezoelectric sensing elements is positioned an equal distance away from a center of the hole, and the annular-shaped piezoelectric sensing element is coaxial with the hole. The structure can include an aircraft in certain implementations.

According to certain implementations of the system, the plurality of first piezoelectric sensing elements and the annular-shaped second piezoelectric sensing element collectively define a first sensing element group and the hole is a first hole. The structure may further include a second hole that is spaced apart from the first hole. The system further includes a second sensing element group that includes a plurality of third piezoelectric sensing elements bonded to the structure and arranged in a generally circular shape about the second hole and an annular-shaped fourth piezoelectric sensing element bonded to the structure and being adjacent the plurality of third piezoelectric sensing elements. One of the plurality of first piezoelectric sensing elements and the annular-shaped second piezoelectric sensing element generates a wave through the structure and one of the plurality of third piezoelectric sensing elements and the annular-shaped fourth piezoelectric sensing element senses the wave after passing through the structure.

In yet another embodiment, a method for detecting damage in a structure includes generating a wave through the structure from one of a plurality of first piezoelectric sensing elements arranged in a generally circular shape or an annular-shaped second piezoelectric sensing element. The method also includes sensing the wave after passing through the structure at other of the plurality of first piezoelectric sensing elements or the annular-shaped second piezoelectric sensing element.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which.

DETAILED DESCRIPTION

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

Figure 1:
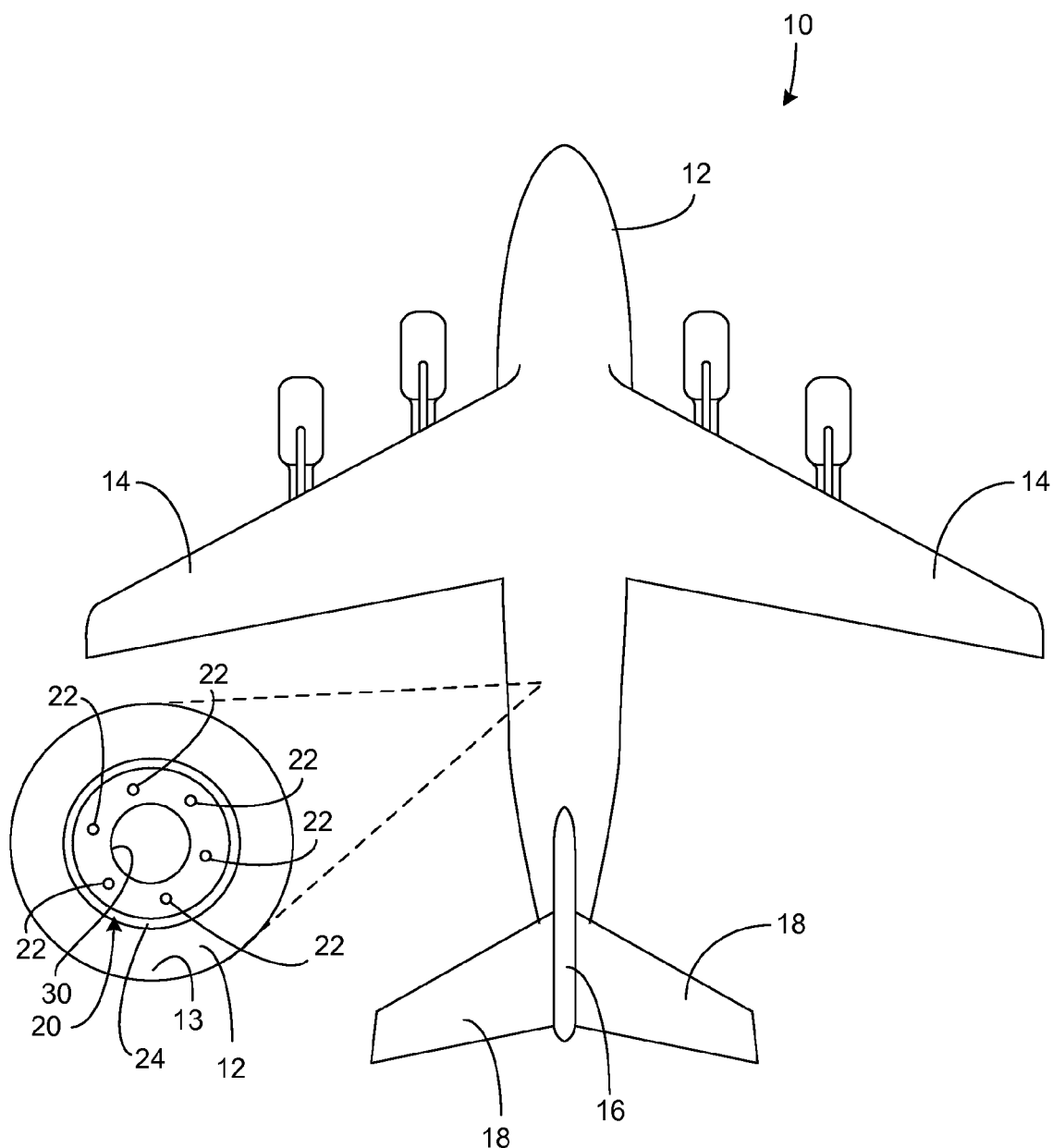
FIG. 1 is a top plan view of an aircraft showing a detailed section of a surface of the aircraft having piezoelectric sensing elements according to one embodiment.

Referring to FIG. 1, one embodiment of an aircraft 10 is shown. The depicted aircraft 10 includes a body 12 or fuselage, a pair of wings 14 coupled to and extending from the body 12, a vertical stabilizer 16 coupled to the body, and a pair of horizontal stabilizers 18 coupled to the body and/or the vertical stabilizer. The aircraft 10 includes features representative of a commercial passenger or military transport aircraft. However, the aircraft 10 can be any of various other types of commercial or non-commercial aircraft, such as personal aircraft, fighter jets, helicopters, spacecraft, and the like. Moreover, although an aircraft is depicted in the illustrated embodiment, in other embodiments, another structure, such as a vehicle (e.g., boat, automobile, etc.) or non-mobile complex structure (e.g., building, bridge, machinery, etc.) can be used without departing from the essence of the present disclosure.

Generally, the body 12, wings 14, vertical stabilizer 16, and horizontal stabilizers 18 of the aircraft 10 each includes an internal frame enveloped by a cover or skin. The cover is coupled to the frame to form an exterior shell of the aircraft. Most commonly, the cover is coupled to the frame using a plurality of fasteners that extend through holes in the cover and engage the frame. The aircraft 10 or other structure may include additional interior layers or structures with holes formed therein to receive fasteners for coupling other components, layers, or structures. Accordingly, although in the depicted embodiment, a hole 30 is shown formed in an outer surface 13 of the body 12 of the aircraft 10 and a sensing element group 20 is shown coupled onto the outer surface 13, in other embodiments, the hole can be formed in an outer or inner surface of another portion of the aircraft, or other structure, and the sensing element group can be coupled onto the outer or inner surface of that portion.

The aircraft 10 may include tens of thousands of holes 30 and associated fasteners in the various portions, components, and sub-structures of the aircraft. The areas adjacent or proximate the holes 30 are susceptible to damage, such as cracking, by virtue of experiencing loads and being exposed to corrosive environmental factors. Although the present disclosure includes apparatus, systems, and methods for detecting damage in any of various structures, such as areas around any holes in the structure, regardless of susceptibility to damage, in some embodiments, the present disclosure is configured to target areas in structures that may be more susceptible to damage than other areas. For example, in some embodiments, only the holes 30 of the aircraft 10 particularly susceptible to damage are monitored for damage using the apparatus, systems, and methods of the present disclosure.

Figure 2:
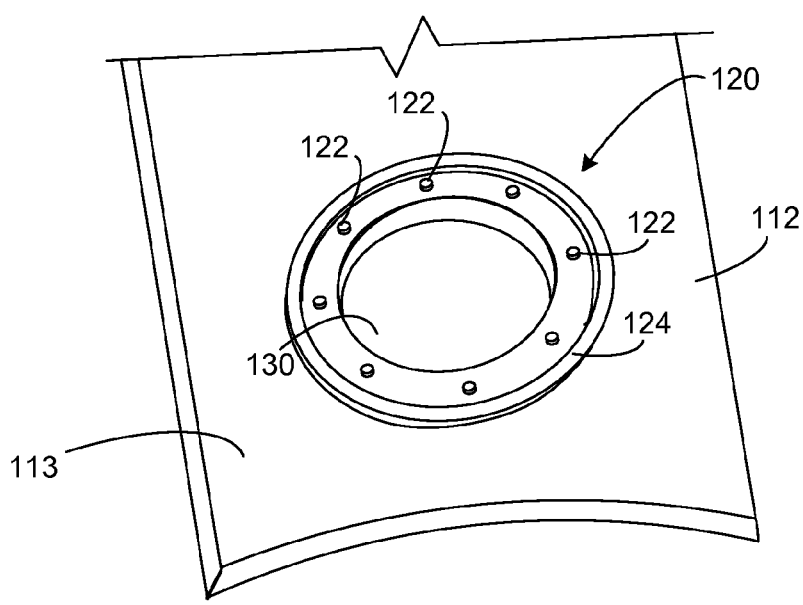
FIG. 2 is a perspective view of a surface of a structure having piezoelectric sensing elements according to one embodiment.

According to one embodiment, the sensing element group 20 includes a plurality of first piezoelectric sensing elements 22 and a second piezoelectric sensing element 24. The sensing element group 20 is coupled to an outer surface 13 of the body 12 of the aircraft 10. The outer surface 13 can be an outer or exterior surface, or an inner or interior surface of the body 12. Again, although a surface of the body of an aircraft is being shown, the surface of any other portion (e.g., wings, stabilizers, etc.) of the aircraft or other structure is equally applicable. The piezoelectric sensing elements 22, 24 can be coupled to the outer surface 13 of the body 12 using any of various coupling techniques. For example, in some implementations, such as FIG. 2 (which shows features analogous to the features of FIG. 1 with like numbers referring to like elements), the piezoelectric sensing elements 122, 124 are bonded onto the surface 113 of the body 112 using a bonding adhesive or other bonding technique. In certain implementations, the aircraft 10 may have additional layers that overlay or are coated onto the outer surface 13 of the body 12 and the piezoelectric sensing elements. Accordingly, in such implementations, the piezoelectric sensing elements 22, 24 can be considered embedded within the body 12. Although less preferable, in some implementations, the piezoelectric sensing elements 22, 24 may be removable from the outer surface 13, and thus may be indirectly and selectively coupled to the surface during periods of testing.

Each of the piezoelectric sensing elements 22, 24 is made from any of various piezoelectric materials. As defined herein, a piezoelectric material is any solid material that accumulates an electric charge when deformed, and deforms when subject to an electric charge. In other words, not only is a piezoelectric material capable of accumulating an electric charge when subject to a force or load that deform or otherwise change the dimensions of the piezoelectric material, but also is capable of changing dimensions to generate a force or load when an electric field is applied to the material. Additionally, piezoelectric materials can include materials that experience deformation when subject to electric and magnetic energy fields, such as electrostrictive and magnetostrictive materials, respectively, but may not accumulate corresponding energy fields when subject to deformation. In this manner, each of the piezoelectric sensing elements 22, 24 can be considered or defined as a transducer. The force or load can be acoustic waves (e.g., lamb waves or elastic waves) that propagate through the body 12 and along the outer surface 13 of the body 12. Accordingly, depending on the configuration of operating mode, a piezoelectric sensing element can act as either an electric accumulator of electrical charge for sensing acoustic waves in the body 12 and along the outer surface 13 of the body, or a wave generator that generates acoustic waves through the body and along the surface of the body.

Generally, the power of the accumulated (sensed) electric charge is directly proportional to the magnitude of the change in dimension caused by an acoustic wave received at the piezoelectric sensing element, thus piezoelectric sensing elements operating as an electric accumulator are able to detect characteristics (e.g., amplitude, frequency, etc.) of received acoustic waves. The inverse is also true, which is that the characteristics of acoustic waves generated by a piezoelectric sensing element are directly proportional to the power of the electrical charge applied to the piezoelectric sensing element, thus piezoelectric sensing elements operating as a wave generator are able to generate acoustic waves with controlled characteristics.

The sensing element group 20 includes a threshold number of first piezoelectric sensing elements 22 or transducers arranged in a generally circular shape. Each piezoelectric sensing element 22 can have any of various shapes and sizes. In the illustrated embodiments, each piezoelectric sensing element 22 has a generally circular, disc-like shape. However, in other embodiments, each piezoelectric sensing element 22 can have a non-circular shape. In some embodiments, the threshold number is at least five. For example, in the illustrated implementation, the sensing element group 20 includes six first piezoelectric sensing elements 22. In other implementations, the sensing element group 20 includes more than six piezoelectric sensing elements 22 arranged in a generally circular shape (see, e.g., FIG. 2). As defined herein, piezoelectric sensing elements 22 are arranged in a generally circular shape when each of the threshold number of piezoelectric sensing elements is positioned a substantially equal distance radially away from a common center point such that a single circle (see, e.g., circle 221 of FIG. 3) extends through an approximate center-point of each element.

The second piezoelectric sensing element or transducer 24 has a generally annular shape. As defined herein, an annular shape can be a generally ring-like shape or a shape forming a continuous ring. In other words, the second piezoelectric sensing element 24 forms a continuous shape that encloses or encircles an open space. In the illustrated embodiments, the second piezoelectric sensing element 24 is circular such that the second piezoelectric sensing element forms a circular ring or band. However, in other embodiments, the second piezoelectric sensing element 24 is non-circular (e.g., ovular, elliptical, square, rectangular, triangular, etc.) to form a non-circular annular ring. Additionally, an annular shape can be defined as forming a portion of a ring or circle. For example, an annular shape need not be a continuous ring in some implementations, but rather can include one or more curved portions that form an entire ring or a portion of a ring.

Additionally, the second piezoelectric sensing element 24 of the sensing element group 20 is positioned adjacent the first piezoelectric sensing elements 22 of the same group. As defined herein, adjacent means proximate, near, or next to in one embodiment. According to some implementations, as shown in FIG. 1, the second piezoelectric sensing element 24 is positioned radially outward of the first piezoelectric sensing elements 22 to surround the first piezoelectric sensing elements. In other implementations, the second piezoelectric sensing element 24 is positioned radially inward of the first piezoelectric sensing elements such that the first piezoelectric sensing elements surround the second piezoelectric sensing element.

In those embodiments with a circular annular-shaped second piezoelectric sensing element 24, the second piezoelectric sensing element 24 can be positioned on the outer surface 13 such that the element 24 is coaxial or centrally aligned with the generally circular shape of the first piezoelectric sensing elements 22. In this manner, the second piezoelectric sensing element 24 is positioned an equal distance radially away from each of the first piezoelectric sensing elements 22.

Figure 3:
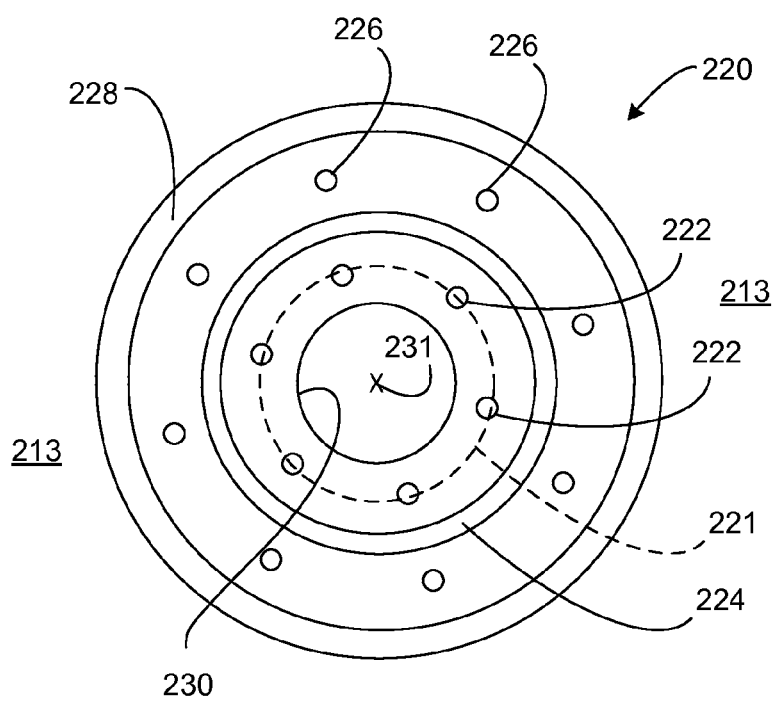
FIG. 3 is a top plan view of a group of piezoelectric sensing elements according to one embodiment.

Referring to FIG. 3, a sensing element group of the present disclosure can include multiple sets of first and second piezoelectric sensing elements. For example, in the illustrated embodiment, the sensing element group 220 (which shows features analogous to the features of FIG. 1 with like numbers referring to like elements) includes a first set of first and second piezoelectric sensing elements 222, 224 and a second set of first and second piezoelectric sensing elements 226, 228 positioned radially outward away from the first set. Similar to the first set of piezoelectric sensing elements 222, 224, the second set of piezoelectric sensing elements 226, 228 includes a plurality of first piezoelectric sensing elements 226 arranged in a generally circular shape, and an annular-shaped second piezoelectric sensing element 228 positioned radially outwardly from the first piezoelectric sensing elements 226. However, while the first set of piezoelectric sensing elements 222, 224 includes six piezoelectric sensing elements 222, the second set of piezoelectric sensing elements 226, 228 includes eight piezoelectric sensing elements 226. In one embodiment, as shown, the generally circular shapes of the first piezoelectric sensing elements 222, 226, and the annular-shaped second piezoelectric sensing elements 224, 228, of the first and second sets are coaxial or centrally aligned with each other.

Figure 4:
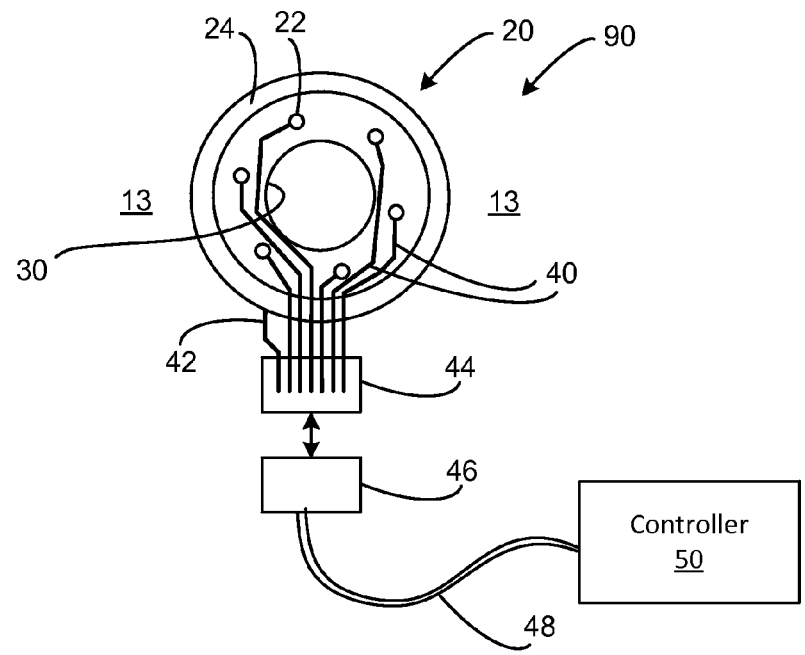
FIG. 4 is a top plan view of another group of piezoelectric sensing elements each electrically coupleable to a controller according to one embodiment.

Referring to FIG. 4, each sensing element group includes a plurality of electrical lead pairs. Each of the electrical lead pairs is electrically coupled to a respective one of the first and second piezoelectric sensing elements. Furthermore, each electrical lead pair includes two electrical leads (e.g., a positive lead and a negative lead) that are electrically coupled together via the corresponding piezoelectric sensing element. In other words, the piezo material of a piezoelectric sensing element is positioned between the positive lead and negative lead of the electrical lead pair. When a voltage is transmitted across the positive lead and negative lead of a pair, the corresponding piezoelectric sensing element strains to produce an acoustic wave.

According to an exemplary embodiment, the sensing element group 20 has a plurality of electrical lead pairs 40 each electrically coupled to a respective one of the first piezoelectric sensing elements 22, and an electrical lead pair 42 electrically coupled to the second piezoelectric sensing element 24. Each electrical lead pair 40, 42 can include two leads, which can be strips, lines, conduits, or the like, made from an electrically conductive material, such as copper, aluminum, etc. In some implementations, the leads of the electrical lead pairs 40, 42 may be wrapped or covered in non-conductive insulation, such as a polymer sleeve, to form a sheathed cable. The electrical lead pairs 40, 42 are coupled to the outer surface 13 of the body 12. In some implementations, the electrical lead pairs 40, 42 are bonded to the outer surface 13 using any of various bonding techniques, such as the same bonding technique used to bond the first and second piezoelectric sensing elements 22, 24 to the surface. The electrical lead pairs 40 may overlay or underlay the second piezoelectric sensing element 24 while remaining electrically isolated from the second piezoelectric sensing element. Additionally, in certain implementations, the aircraft 10 may have additional layers that overlay or are coated onto the outer surface 13 of the body 12 and at least a portion of the electrical lead pairs 40, 42.

The sensing element group 20 also includes an electrical lead interface 44. Each electrical lead pair 40, 42 extends from a first end coupled to respective first and second piezoelectric sensing elements to a second end forming at least part of the electrical lead interface 44. In certain implementations, the electrical lead interface 44 includes an electrical connector that is electrically coupled to the second ends of the leads of the electrical lead pairs 40, 42. In some implementations, the electrical lead interface 44 is a platform or area that contains the second ends of the leads of the electrical lead pairs 40, 42 in a fixed or uniform manner. The electrical lead interface 44, and in some implementations the second ends of the leads of the electrical lead pairs 40, 42 themselves, are physically accessible in situ by a user. In implementations where the outer surface 13 is an outer surface, the electrical lead interface 44 and electrical lead pairs 40, 42 are physically accessible in situ by a user external to the outer surface. Similarly, where the outer surface 13 is an inner surface, the electrical lead interface 44 and electrical lead pairs 40, 42 are physically accessible in situ by a user internal to the inner surface. The electrical lead interface 44 may be fitted with a removable or movable cover that can be engaged to access the electrical lead interface 44.

Referring again to FIG. 4, the sensing element group 20 can form part of a damage detection system 90. The damage detection system 90 also includes a controller 50 that is electrically communicable with the sensing element group 20 via an electrical lead interface 46 and electrical communication line 48 or wire. The electrical lead interface 46 interfaces with the plurality of electrical lead pairs 40, 42 directly or through the electrical lead interface 44. For example, in one implementation, the electrical lead interface 46 may include a connector that interfaces with a connector of the electrical lead interface 44. When interfaced with the plurality of electrical lead pairs 40, 42, the controller 50 can send electrical signals to and receive electrical signals from the first and second piezoelectric sensing elements 22, 24 via the electrical communication line 48.

Figure 6:
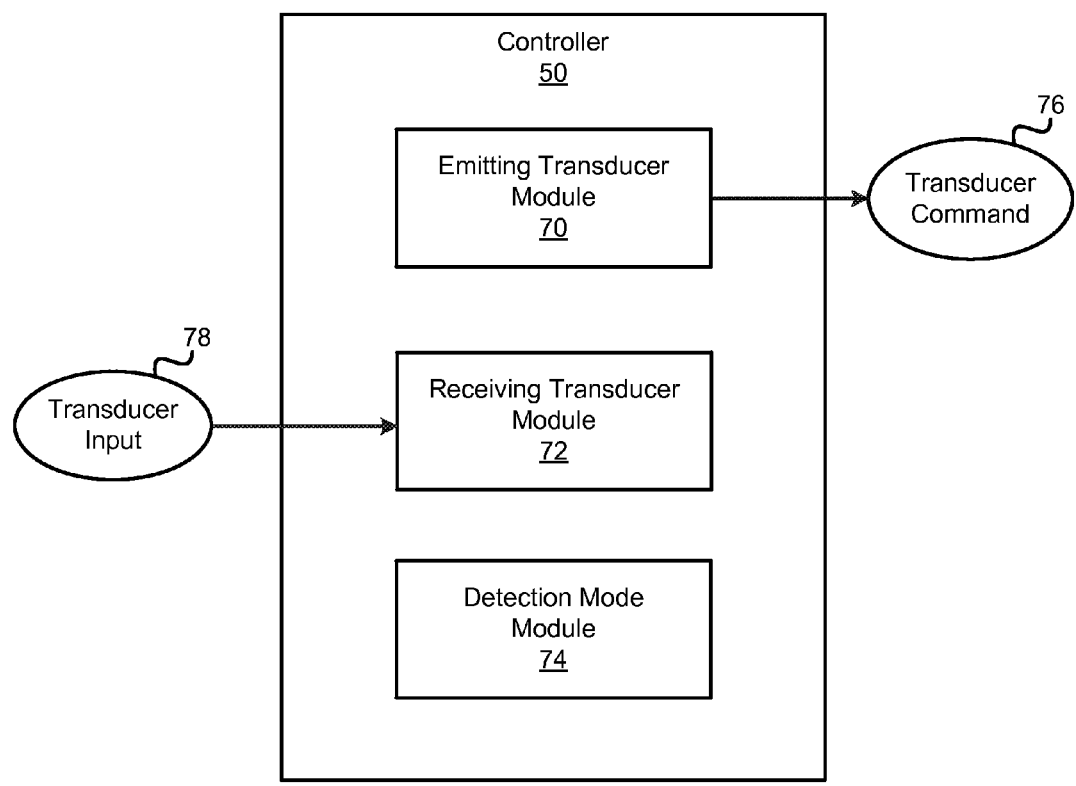
FIG. 6 is a schematic block diagram of a controller for controlling a group of piezoelectric sensing elements according to one embodiment.

As shown in FIG. 6, according to one embodiment, the controller 50 includes an emitting transducer module 70, a receiving transducer module 72, and a detection mode module 74. The emitting transducer module 70 is configured to generate a transducer command 76 that commands an electrical pulse with characteristics corresponding to an acoustic wave with desired characteristics be sent to the one or more piezoelectric sensing elements acting as the wave generator. The transducer command 76 may be sent to an electrical pulse generator that is separate or integral with the controller 50 that generates the desired electrical pulse(s), and transmits the electrical pulse(s) to the wave generating piezoelectric sensing element(s), in response to receiving the transducer command 76. The electrical pulse(s) are sent to the wave generating piezoelectric sensing element(s) from the generator via the electrical communication line 48 and electrical lead(s) associated with the wave generating piezoelectric sensing element(s).

In some embodiments, the annular-shaped second piezoelectric sensing element 24 acts as the wave generator. Accordingly, in response to receiving the transducer command 76, the electrical pulse generator transmits electrical pulses to the second piezoelectric sensing element 24. Correspondingly, in response to receiving the electrical pulses from the electrical pulse generator, the second piezoelectric sensing element 24 deforms to generate an acoustic wave with the desired characteristics that propagates through the body 12 and along the outer surface 13 of the body. Because the second piezoelectric sensing element 24 has an annular shape, the acoustic wave generated by the second piezoelectric sensing element more uniformly and broadly propagates through the body 12 and along the outer surface 13 with reduced attenuation compared to multiple spaced-apart piezoelectric sensing discs.

The receiving transducer module 72 is configured to receive transducer input 78 from the one or more piezoelectric sensing elements acting as the electric accumulator. As discussed above, upon deformation due to the exposure to acoustic waves, the piezoelectric sensing elements accumulate electrical charge that is approximately proportional to the magnitude of the acoustic waves. The transducer input 78 includes signals representative of the accumulated electrical charge, and thus representative of the magnitude of the acoustic waves. The transducer input 78 is communicated from the piezoelectric sensing elements to the controller 50 via the electrical lead(s) associated with the one or more piezoelectric sensing elements acting as the electric accumulator and the electrical communication line 48.

In some embodiments, the plurality of first piezoelectric sensing elements 22 arranged in the generally circular shape act as the electric accumulators. Accordingly, after being exposed to acoustic waves generated by the annular-shaped second piezoelectric sensing element 24, the plurality of first piezoelectric sensing elements 22 generate and transmit transducer input 78 back to the controller 50. Because the acoustic waves are generated by an annular-shaped second piezoelectric sensing element 24, and the first piezoelectric sensing elements 22 are arranged in a generally circular shape corresponding to the shape of the second piezoelectric sensing element, the first piezoelectric sensing elements monitor and detect a wider portion (e.g., area) of the body 12 and outer surface 13 compared to traditional approaches. Moreover, positioning the second piezoelectric sensing elements 22 uniformly about a point and equidistant from that point, such as in a circular arrangement, promotes accuracy and broader damage detection coverage.

According to some embodiments, the receiving transducer module 72, or separate analysis module (not shown) utilizes the transducer input 78 to detect the presence of damage in the structure (e.g., the body 12 and/or the outer surface 13). The receiving transducer module 72 can use any of various methods and/or apply any of various algorithms for detecting damage based on the transducer input 78. In certain embodiments, the transducer module 72 detects damage by applying the transducer input 78 to a baselineless model without relying on predetermined or known baselines.

However, in yet some embodiments, the transducer module 72 detects damage by applying the transducer input 78 to a baseline model by relying on predetermined or known baseline waveforms. For example, in one embodiment, the receiving transducer module 72 compares the transducer input 78 with an expected transducer input or baseline input to detect the presence of damage in the structure. The expected transducer input represents the input expected to be received in response to hypothetical acoustic waves with specific characteristics passing through a structure without damage. Accordingly, variations in the actual transducer input 78 compared to the expected transducer input indicates abnormalities or damage (e.g., cracking) in the structure. For a proper comparison, the transducer command 76 generated by the emitting transducer module 70 commands the annular-shaped second piezoelectric sensing element 24, or wave generator, to generate in the structure actual acoustic waves with characteristics matching the hypothetical acoustic waves.

Although, in the above embodiment, the plurality of first piezoelectric sensing elements 22 each act as an electrical accumulator and the annular-shaped second piezoelectric sensing element 24 acts as the wave generator, in other embodiments, the plurality of first piezoelectric sensing elements 22 each may act as a wave generators and the second piezoelectric sensing element 24 may act as the electrical accumulator.

As discussed above, various portions, components, and sub-structures of a structure can be more susceptible to damage than others. Accordingly, in certain embodiments, a sensing element group 20 can be positioned near or adjacent a susceptible portion of a structure to more accurately and comprehensively detect damage on or near the portion. For example, many holes formed in structures are particularly susceptible to cracks that form at and emanate from the holes. For this reason, in the illustrated embodiments, the sensing element group 20 is positioned near or adjacent the hole 30 formed in the body 12 of the aircraft 10. More specifically, and for enhanced results, the sensing element group 20 is positioned concentrically around the hole 30 such that centers of the circular shape of the first piezoelectric sensing elements 22 and annular-shaped second piezoelectric sensing element 24 are centrally aligned or coaxial with a central axis of the hole 30 (see, e.g., central axis 231 of the hole 230 shown in FIG. 3). In this configuration, each of the first piezoelectric sensing elements 22 are positioned an equal distance radially away from the central axis of the hole, and the peripheries of the second piezoelectric sensing element 24 is spaced the same radial distance away from the central axis of the hole. Moreover, in this configuration, the sensing element group 20 is positioned to more uniformly, broadly, and accurately detect damage, including cracks, in the immediate space around the hole 30.

Although the above embodiment is described and shown with reference to the position of the sensing element group 20 around a hole 30 formed in an aircraft 10 to detect damage around the hold, in other embodiments, the sensing element group can be placed about another portion, component, or sub-structure of an aircraft or other structure to detect damage about the portion, component, or sub-structure in the same or similar manner.

Figure 5:
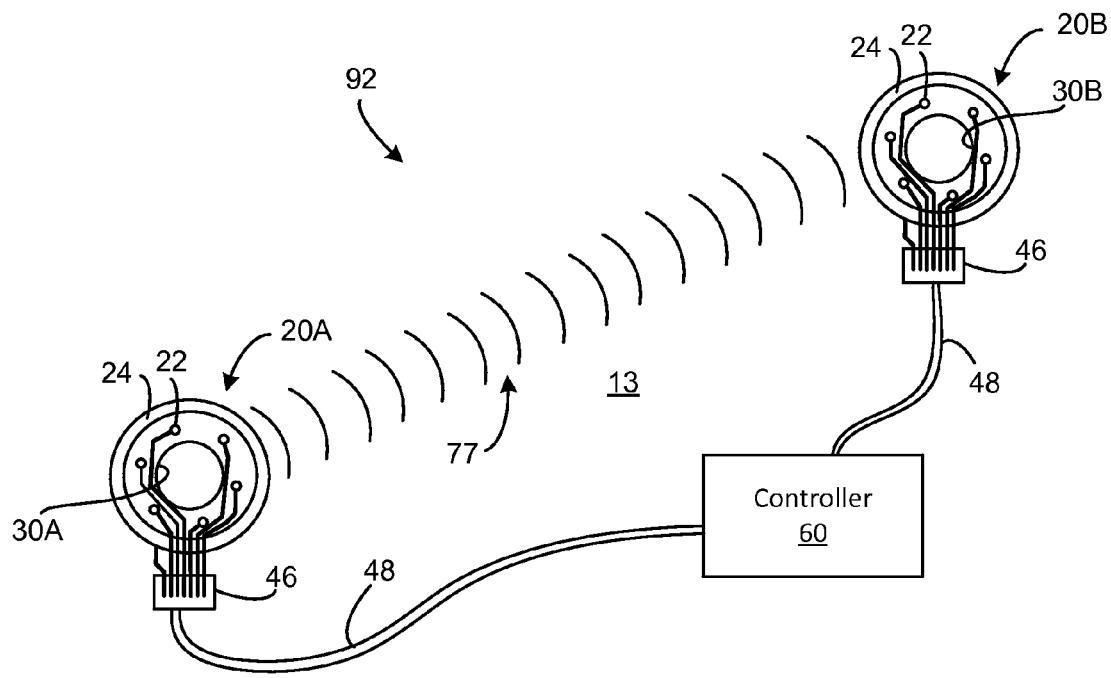
FIG. 5 is a top plan view of first and second groups of piezoelectric sensing elements spaced apart on a surface of a structure according to one embodiment.

Additionally, in certain embodiments, multiple, spaced-apart, sensing element groups can be configured to detect not only damage in the structure about which each sensing element group is positioned, but also damage in the structure between the sensing element groups. For example, as shown in FIG. 5, a damage detection system 92 includes at least two sensing element groups 20A, 20B each surrounding respective holes 30A, 30B formed in the outer surface 13. Each sensing element group 20A, 20B is configured to individually and independently detect damage in the structure (e.g., body 12 and outer surface 13) about the respective holes 30A, 30B (e.g., cracks emanating from the holes) as described above.

As shown, the damage detection system 92 includes a controller 60 and separate electrical lead interfaces 46 and electrical communication lines 48 that separately facilitate the communication between the sensing element groups 20A, 20B, respectively, and the controller 60. The controller 60 has features analogous to the features of the controller 50 of FIG. 6. More specifically, the controller 60 includes an emitting transducer module 70 and receiving transducer module 72 that separately control the generation and detection of acoustic waves for each sensing element group 20A, 20B in a first mode of operation. However, in a second mode of operation, the emitting transducer module 70 controls the generation of acoustic waves 77 from one of the sensing element groups 20A, 20B, and the receiving transducer module 72 controls the detection of the generated acoustic waves by the other of the sensing element groups. For example, in the illustrated embodiment, the emitting transducer module 70 controls the sensing element group 20A to generate the acoustic waves 77, and the receiving transducer module 72 controls the sensing element group 20B to receive the acoustic waves 77. The emitting transducer module 70 may activate the second piezoelectric sensing element 24 of the sensing element group 20A to generate the acoustic waves, activate one or more of the first piezoelectric sensing elements 22 of the sensing element group 20A to generate the acoustic waves, or activate both the first and second piezoelectric sensing elements of the sensing element group 20A to generate the acoustic waves.

The receiving transducer module 72 of the controller 60, or separate analysis module, then applies the transducer input 78 from the sensing element group 20B according to one of various methods to detect the presence of damage in the portion of the structure between the holes 30A, 30B. According to one implementation, the receiving transducer module 72 compares the transducer input 78 from the sensing element group 20B with an expected transducer input to detect the presence of damage in the portion of the structure between the holes 30A, 30B. In this implementation, the expected transducer input in the second mode represents the input expected to be received in response to hypothetical acoustic waves with specific characteristics passing through a portion of the structure between the holes 30A, 30B that does not have damage. For a proper comparison, the transducer command 76 generated by the emitting transducer module 70 commands the sensing element group 20A, which acts as the wave generator, to generate in the structure between the holes 30A, 30B actual acoustic waves with characteristics matching the hypothetical acoustic waves.

In some embodiments, the controller 60 includes a detection mode module 74 that selectively switches operation of the emitting transducer module 70 and receiving transducer module 72 between the first and second modes. According to certain implementations, the detection mode module 74 may operate the modules 70, 72 first in the first mode to detect damage near and just around certain features in the structure, such as the holes 30A, 30B, and then switch to operation in the second mode to detect damage in the structure between the features or holes. Alternatively, the detection mode module 74 may operate the modules 70, 72 first in the second mode to detect damage in the structure between the features or holes, and then in the first mode to detect damage near and just around the certain features in the structure. Also, in some implementations, the detection mode module 74 may operate the modules 70, 72 in only the first or second mode as desired.

Although the above embodiment shown in relation to FIG. 5 shows one sensing element group acting as a wave generator and one sensing element group acting as an acoustic wave receiver or detector, in other embodiments, a system can have more than one sensing element group acting as wave generators and more than one sensing element group acting as wave detectors.

Figure 7:
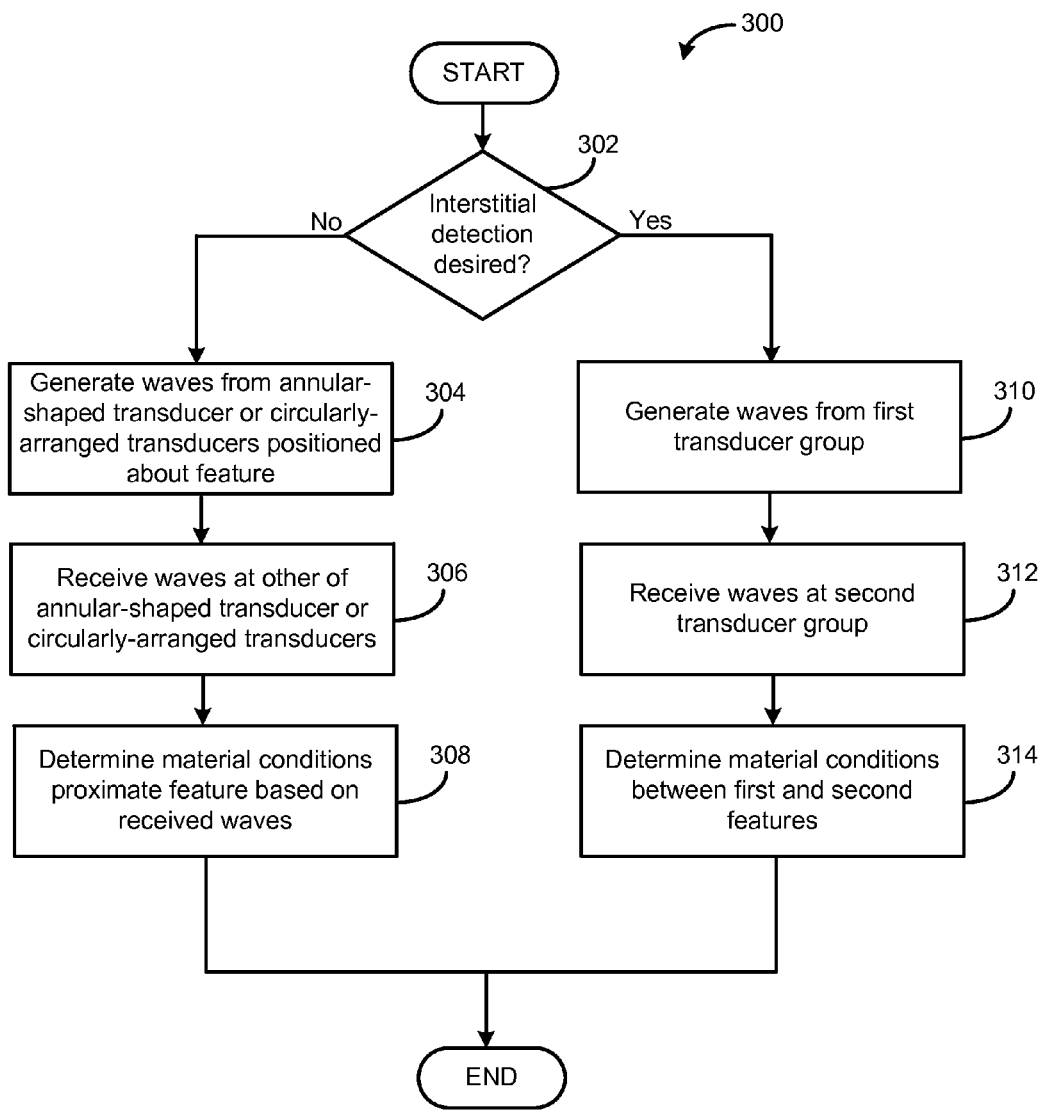
FIG. 7 is a schematic flow diagram of a method for detecting damage in a structure according to one embodiment.

Referring to FIG. 7, according to one embodiment, a method 300 for detecting damage in a structure can be executed by the systems and apparatus described herein, or other systems and apparatus. The method 300 begins by determining whether interstitial detection is desired at 302. Interstitial detection can be defined as the detection of damage in structure between sensing element groups, such as described and shown in relation to the damage detection system 92 of FIG. 5. If interstitial detection is not desired at 302 (i.e., detection of damage in the immediate feature (e.g., hole) about which a sensing element group surrounds is desired), then the method 300 proceeds to generate acoustic waves from one of the annular-shaped transducer (e.g., sensing element) or plurality of circularly-arranged transducers of a sensing element group at 304. Additionally, the method 300 receives or detects the generated acoustic waves at other of the annular-shaped transducer (e.g., sensing element) or plurality of circularly-arranged transducers of the sensing element group at 306. Then, the method 300 determines material conditions (e.g., damage) proximate or immediately surrounding the structure based on the characteristics of the received waves at 308.

However, if interstitial detection is desired at 302, then the method 300 proceeds to generate acoustic waves from a first transducer group (e.g., first sensing element group) at 310, and receives or detects the generated acoustic waves at a second transducer group at 312. The second transducer group is spaced apart from the first transducer group. The method 300 also includes determining material conditions in the structure between the first and second transducer groups (e.g., between the first and second features about which the first and second transducer groups surround) at 314.

Figure 8:
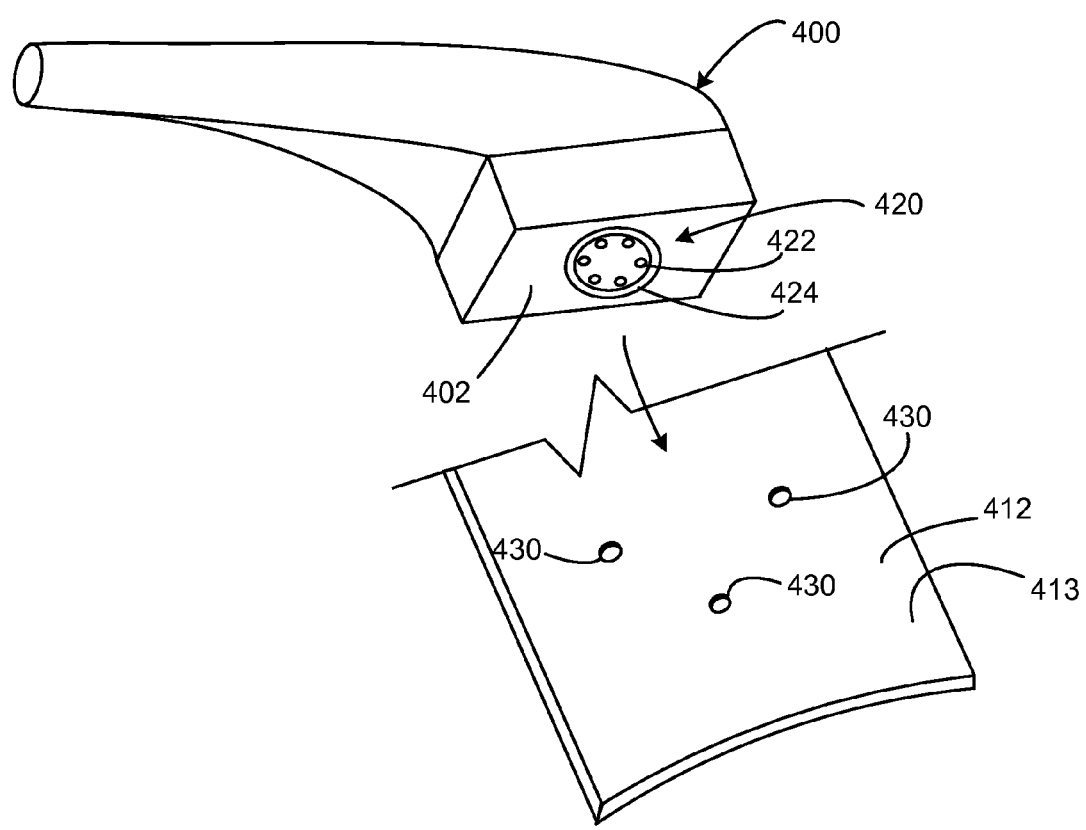
FIG. 8 is a perspective view of a mobile test head having a group of piezoelectric sensing elements, with the test head being positioned relative to a surface of a structure, according to one embodiment.

Referring now to FIG. 8, a sensing element group 420 can be integrated into a mobile test head 400 of a damage detecting system. The sensing element group 420 includes a plurality of first piezoelectric sensing elements 422 arranged in a circular shape on a scanning surface 402 of the mobile test head 400. Additionally, the sensing element group 420 includes an annular-shaped second piezoelectric sensing element 424 on the scanning surface 402 of the head. The annular-shaped second piezoelectric sensing element 424 is positioned around and concentric with the circular shape of the first piezoelectric sensing elements 422 in a manner as described above in relation to the sensing element group 20 of FIG. 1. The scanning surface 402 of the mobile test head 400 can be brought into at least close proximity with a surface 413 of a structure 412 as shown by the directional arrow. In one implementation, the scanning surface 402 is placed in contact with the surface 413. The structure 412 includes at least one hole 430 or other feature of interest formed in the surface 413 of the structure.

In operation, the mobile test head 400 can be moved into positioned above one of the holes 430 such that a central axis of the hole is approximately coaxial with the piezoelectric sensing elements of the sensing element group 420. In some implementations, the mobile test head 400 may have a positioning system that determines and notifies a user when the mobile test head is properly positioned over a hole. When properly positioned over a hole 30 to be tested, the mobile test head 400 is operable to activate the annular-shaped second piezoelectric sensing element 424 to generate an acoustic wave in the structure 412 around the hole 30 to be tested, and receive input regarding the characteristics of the generated acoustic wave from the plurality of first piezoelectric sensing elements 422. As described above, the roles of the first piezoelectric sensing elements 422 and the second piezoelectric sensing element 424 can be reversed in some embodiments. The mobile test head 400, or a controller coupled to the test head, can be equipped to compare the input received from the plurality of first piezoelectric sensing elements 422 with an expected or baseline input to detect the presence of damage in the structure 412 in a manner similar to that described above.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two."

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

As will be appreciated by one skilled in the art, aspects of the present invention can be embodied as a system, method, and/or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present invention may take the form of a computer program product embodied in one or more computer readable medium(s) having program code embodied thereon.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the program code may be stored and/or propagated on in one or more computer readable medium(s).

The computer readable medium may be a tangible computer readable storage medium storing the program code. The computer readable storage medium may be, for example, but not limited to, an electronic, magnetic, optical, electromagnetic, infrared, holographic, micromechanical, or semiconductor system, apparatus, or device, or any suitable combination of the foregoing.

More specific examples of the computer readable storage medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store program code for use by and/or in connection with an instruction execution system, apparatus, or device.

The computer readable medium may also be a computer readable signal medium. A computer readable signal medium may include a propagated data signal with program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport program code for use by or in connection with an instruction execution system, apparatus, or device. Program code embodied on a computer readable signal medium may be transmitted using any appropriate medium, including but not limited to wire-line, optical fiber, Radio Frequency (RF), or the like, or any suitable combination of the foregoing In one embodiment, the computer readable medium may comprise a combination of one or more computer readable storage mediums and one or more computer readable signal mediums. For example, program code may be both propagated as an electro-magnetic signal through a fiber optic cable for execution by a processor and stored on RAM storage device for execution by the processor.

Program code for carrying out operations for aspects of the present invention may be written in any combination of one or more programming languages, including an object oriented programming language such as Java, Smalltalk, C++, PHP or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The computer program product may be shared, simultaneously serving multiple customers in a flexible, automated fashion. The computer program product may be standardized, requiring little customization and scalable, providing capacity on demand in a pay-as-you-go model.

The computer program product may be stored on a shared file system accessible from one or more servers. The computer program product may be executed via transactions that contain data and server processing requests that use Central Processor Unit (CPU) units on the accessed server. CPU units may be units of time such as minutes, seconds, hours on the central processor of the server. Additionally the accessed server may make requests of other servers that require CPU units. CPU units are an example that represents but one measurement of use. Other measurements of use include but are not limited to network bandwidth, memory usage, storage usage, packet transfers, complete transactions etc.

Aspects of the embodiments may be described above with reference to schematic flowchart diagrams and/or schematic block diagrams of methods, apparatuses, systems, and computer program products according to embodiments of the invention. It will be understood that each block of the schematic flowchart diagrams and/or schematic block diagrams, and combinations of blocks in the schematic flowchart diagrams and/or schematic block diagrams, can be implemented by program code. The program code may be provided to a processor of a general purpose computer, special purpose computer, sequencer, or other programmable data processing apparatus to produce a machine, such that the instructions, which execute via the processor of the computer or other programmable data processing apparatus, create means for implementing the functions/acts specified in the schematic flowchart diagrams and/or schematic block diagrams block or blocks.

The program code may also be stored in a computer readable medium that can direct a computer, other programmable data processing apparatus, or other devices to function in a particular manner, such that the instructions stored in the computer readable medium produce an article of manufacture including instructions which implement the function/act specified in the schematic flowchart diagrams and/or schematic block diagrams block or blocks.

The program code may also be loaded onto a computer, other programmable data processing apparatus, or other devices to cause a series of operational steps to be performed on the computer, other programmable apparatus or other devices to produce a computer implemented process such that the program code which executed on the computer or other programmable apparatus provide processes for implementing the functions/acts specified in the flowchart and/or block diagram block or blocks.

The schematic flowchart diagrams and/or schematic block diagrams in the Figures illustrate the architecture, functionality, and operation of possible implementations of apparatuses, systems, methods and computer program products according to various embodiments of the present invention. In this regard, each block in the schematic flowchart diagrams and/or schematic block diagrams may represent a module, segment, or portion of code, which comprises one or more executable instructions of the program code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

The present subject matter may be embodied in other specific forms without departing from its spirit or essential characteristics. The described embodiments are to be considered in all respects only as illustrative and not restrictive. All changes which come within the meaning and range of equivalency of the claims are to be embraced within their scope.

What is claimed is:

1. An apparatus for detecting damage in a structure comprising a hole, comprising:
   a plurality of first piezoelectric sensing elements arranged in a generally circular shape about the hole; and
   an annular-shaped second piezoelectric sensing element positioned adjacent the plurality of first piezoelectric sensing elements and about the hole;
   wherein one of the plurality of first piezoelectric sensing elements or the annular-shaped second piezoelectric sensing element is configured to generate a wave through the structure and other of the plurality of first piezoelectric sensing elements or the annular-shaped second piezoelectric sensing element is configured to sense the wave after passing through the structure adjacent the hole.

2. The apparatus of claim 1, wherein the annular-shaped second piezoelectric sensing element surrounds the plurality of first piezoelectric sensing elements.

3. The apparatus of claim 1, further comprising:
   a plurality of third piezoelectric sensing elements arranged in a generally circular shape surrounding the annular-shaped second piezoelectric sensing element; and
   an annular-shaped fourth piezoelectric sensing element that surrounds the plurality of third piezoelectric sensing elements.

4. The apparatus of claim 1, wherein the plurality of first piezoelectric sensing elements comprises at least five piezoelectric sensing elements.

5. The apparatus of claim 1, wherein the plurality of first piezoelectric sensing elements and the annular-shaped second piezoelectric sensing element are bonded onto the structure.

6. The apparatus of claim 5, further comprising a plurality of electrical lead pairs bonded to the structure, wherein each of the plurality of electrical lead pairs comprises at least two electrical leads electrically coupled to a respective one of the first and second piezoelectric sensing elements.

7. The apparatus of claim 1, further comprising a mobile test head movable along the structure, the mobile test head comprising the plurality of first piezoelectric sensing elements and the annular-shaped second piezoelectric sensing element.

8. The apparatus of claim 1, wherein the plurality of first piezoelectric sensing elements and the annular-shaped second piezoelectric sensing element collectively define a first sensing element group, the apparatus further comprising a second sensing element group spaced apart from the first sensing element group, the second sensing element group comprising a plurality of third piezoelectric sensing elements arranged in a generally circular shape and an annular-shaped fourth piezoelectric sensing element positioned adjacent the plurality of third piezoelectric sensing elements, and wherein one of the plurality of first piezoelectric sensing elements and the annular-shaped second piezoelectric sensing element is configured to generate a wave through the structure and one of the plurality of third piezoelectric sensing elements and the annular-shaped fourth piezoelectric sensing element is configured to sense the wave after passing through the structure.

9. The apparatus of claim 8, wherein the first sensing element group is centered around a first hole formed in the structure and the second sensing element group is centered around a second hole formed in the structure.

10. The apparatus of claim 8, further comprising a controller configured to selectively switch between operation in a first mode and second mode, wherein in the first mode the controller activates the first sensing element group to generate a first wave and receives input from the first sensing element group regarding characteristics of the first wave and activates the second sensing element group to generate a second wave and receives input from the second sensing element group regarding characteristics of the second wave, and wherein in the second mode the controller activates the first sensing element group to generate a third wave and receives input from the second sensing element group regarding characteristics of the third wave.

11. The apparatus of claim 1, further comprising a controller configured to activate the one of the plurality of first piezoelectric sensing elements or the annular-shaped second piezoelectric sensing element to generate the wave, and to receive input from other of the plurality of first piezoelectric sensing elements or the annular-shaped second piezoelectric sensing element that sense the wave after passing through the structure.

12. The apparatus of claim 11, further comprising a plurality of electrical lead pairs bonded to the structure, wherein each of the plurality of electrical lead pairs comprises at least two electrical leads electrically coupled to a respective one of the first and second piezoelectric sensing elements, and wherein the controller comprises an electrical lead interface that interfaces with the plurality of electrical lead pairs to send electrical signals to or receive electrical signals from the plurality of first piezoelectric sensing elements and the annular-shaped second piezoelectric sensing element.

13. The apparatus of claim 1, wherein the annular-shaped second piezoelectric sensing element is substantially coaxial with the generally circular shape of the plurality of first piezoelectric sensing elements.

14. The apparatus of claim 13, wherein the annular-shaped second piezoelectric sensing element is positioned radially outwardly away from the plurality of piezoelectric sensing elements.

15. The apparatus of claim 1, wherein each of the first piezoelectric sensing elements comprises a piezoelectric sensor disc.

16. A system, comprising:
a structure comprising a hole;
a plurality of first piezoelectric sensing elements arranged in a generally circular shape about the hole; and
an annular-shaped second piezoelectric sensing element positioned adjacent the plurality of first piezoelectric sensing elements and about the hole;
wherein one of the plurality of first piezoelectric sensing elements or the annular-shaped second piezoelectric sensing element is configured to generate a wave through the structure and other of the plurality of first piezoelectric sensing elements or the annular-shaped second piezoelectric sensing element is configured to sense the wave after passing through the structure adjacent the hole.

17. The system of claim 16, wherein each of the plurality of first piezoelectric sensing elements is positioned an equal distance away from a center of the hole, and the annular-shaped piezoelectric sensing element is coaxial with the hole.

18. The system of claim 16, wherein the structure comprises an aircraft.

19. The system of claim 16, wherein the plurality of first piezoelectric sensing elements and the annular-shaped second piezoelectric sensing element collectively define a first sensing element group and the hole is a first hole, the structure further comprising a second hole spaced apart from the first hole, and the system further comprising a second sensing element group comprising a plurality of third piezoelectric sensing elements bonded to the structure and arranged in a generally circular shape about the second hole and an annular-shaped fourth piezoelectric sensing element bonded to the structure and being adjacent the plurality of third piezoelectric sensing elements, and wherein one of the plurality of first piezoelectric sensing elements and the annular-shaped second piezoelectric sensing element is configured to generate a wave through the structure and one of the plurality of third piezoelectric sensing elements and the annular-shaped fourth piezoelectric sensing element is configured to sense the wave after passing through the structure.

20. A method for detecting damage in a structure comprising a hole, the method comprising:
generating a wave through the structure from one of a plurality of first piezoelectric sensing elements arranged in a generally circular shape about the hole or an annular-shaped second piezoelectric sensing element positioned adjacent the plurality of first piezoelectric sensing elements and about the hole; and
sensing the wave after passing through the structure adjacent the hole at other of the plurality of first piezoelectric sensing elements or the annular-shaped second piezoelectric sensing element.

* * * * *